(12) United States Patent
Kochinke et al.

(10) Patent No.: US 8,747,820 B2
(45) Date of Patent: Jun. 10, 2014

(54) METHODS FOR TREATING CONDITIONS OF THE NAIL UNIT

(71) Applicant: Hallux, Inc., Laguna Hills, CA (US)

(72) Inventors: Frank Kochinke, San Jose, CA (US); Corinne Bright, Los Gatos, CA (US)

(73) Assignee: Hallux, Inc., Laguna Hills, CA (US)

( * ) Notice: Subject to any disclaimer, the term of this patent is extended or adjusted under 35 U.S.C. 154(b) by 0 days.

(21) Appl. No.: 14/061,478

(22) Filed: Oct. 23, 2013

(65) Prior Publication Data

US 2014/0050772 A1  Feb. 20, 2014

Related U.S. Application Data

(60) Division of application No. 12/985,996, filed on Jan. 6, 2011, now Pat. No. 8,591,870, which is a continuation of application No. 11/441,747, filed on May 25, 2006, now abandoned, which is a continuation-in-part of application No. 11/302,014, filed on Dec. 12, 2005, now abandoned.

(60) Provisional application No. 60/593,106, filed on Dec. 10, 2004.

(51) Int. Cl.
*A61F 2/00* (2006.01)
*A61K 9/14* (2006.01)

(52) U.S. Cl.
USPC .............. 424/61; 424/443; 424/471; 424/486

(58) Field of Classification Search
USPC ........ 424/61, 443, 471, 486; 514/159, 253.07
See application file for complete search history.

(56) References Cited

U.S. PATENT DOCUMENTS

| | | | |
|---|---|---|---|
| 4,180,058 A | 12/1979 | Brem | |
| 4,957,730 A | 9/1990 | Bohn et al. | |
| 5,002,769 A | 3/1991 | Friedman | |
| 5,464,610 A | 11/1995 | Hayes, Jr. et al. | |
| 5,705,181 A | 1/1998 | Copper et al. | |
| 5,814,305 A | 9/1998 | Laugier et al. | |
| 5,916,545 A | 6/1999 | Burnett et al. | |
| 5,947,956 A | 9/1999 | Karell | |
| 5,993,790 A | 11/1999 | Strauss | |
| 6,231,840 B1 | 5/2001 | Buck | |
| 6,391,879 B1 | 5/2002 | Reeves | |
| 6,495,124 B1 | 12/2002 | Samour | |
| 6,517,863 B1 | 2/2003 | LaTorre et al. | |
| 6,676,953 B2 | 1/2004 | Hexamer | |
| 6,727,401 B1 | 4/2004 | Venkateshwaran et al. | |
| 6,846,837 B2 | 1/2005 | Maibach et al. | |
| 7,138,179 B2 | 11/2006 | Kim et al. | |
| 2002/0164374 A1 | 11/2002 | Jackson et al. | |
| 2003/0049307 A1 | 3/2003 | Gyurik | |
| 2003/0072807 A1 | 4/2003 | Wong et al. | |
| 2003/0118649 A1* | 6/2003 | Gao et al. ...................... | 424/471 |
| 2003/0130225 A1 | 7/2003 | Ahmad et al. | |
| 2003/0235541 A1 | 12/2003 | Maibach et al. | |
| 2004/0062733 A1* | 4/2004 | Birnbaum ....................... | 424/61 |
| 2004/0137059 A1 | 7/2004 | Nivaggioli et al. | |
| 2004/0197280 A1 | 10/2004 | Repka | |
| 2005/0042293 A1* | 2/2005 | Jackson et al. ................. | 424/486 |
| 2006/0067898 A1 | 3/2006 | Kepka et al. | |
| 2006/0153786 A1 | 7/2006 | Kochinke et al. | |
| 2006/0204548 A1 | 9/2006 | Nivaggioli et al. | |
| 2006/0275230 A1 | 12/2006 | Kochinke et al. | |
| 2008/0132442 A1 | 6/2008 | Kochinke et al. | |
| 2009/0004272 A1 | 1/2009 | Gibson et al. | |

FOREIGN PATENT DOCUMENTS

| | | |
|---|---|---|
| AU | 742061 B2 | 6/1998 |
| CA | 2326057 A1 | 5/2001 |
| DE | 19836436 A1 | 3/1999 |
| EP | 0952171 A2 | 10/1999 |
| EP | 1477187 A1 | 11/2004 |
| GR | 30306696 | 12/2001 |
| JP | 8231430 A | 9/1996 |
| KR | 20010044625 | 6/2001 |
| KR | 20010046941 | 6/2001 |
| RU | 2062607 C1 | 6/1996 |
| RU | 2083224 C1 | 7/1997 |
| RU | 2127118 C1 | 3/1999 |
| RU | 2134568 C1 | 8/1999 |
| RU | 2146139 C1 | 3/2000 |
| RU | 2159148 C2 | 11/2000 |
| RU | 2161502 C2 | 1/2001 |
| RU | 2164418 C2 | 3/2001 |
| RU | 2165265 C2 | 4/2001 |
| RU | 2176525 C2 | 12/2001 |
| RU | 2196555 C2 | 1/2003 |
| RU | 2197964 C2 | 2/2003 |
| RU | 2207845 C2 | 7/2003 |
| RU | 2001129096 C2 | 9/2003 |
| RU | 2215542 C2 | 11/2003 |
| RU | 2232779 C2 | 7/2004 |
| RU | 2234337 C2 | 8/2004 |
| SU | 1122323 A | 11/1984 |
| WO | WO 89/08449 A1 | 9/1989 |

(Continued)

OTHER PUBLICATIONS

Encyclopedic Dictionary of Medical Terms, "Meditsina," pp. 326 and 807, 5 pgs. (2001) English translation included.

Favre et al., "Comparison of In Vitro Activities of 17 Antifungal Drugs Against a Panel of 20 Dermatophytes by Using a Microdilution Assay," Journal of Clinical Microbiology, vol. 41, No. 10, pp. 4817-4819 (2003).

Final Office Action mailed on Aug. 29, 2008 for U.S. Appl. No. 11/302,014, 10 pgs., filed Dec. 12, 2005.

(Continued)

*Primary Examiner* — Michael G Hartley
*Assistant Examiner* — Jagadishwar Samala
(74) *Attorney, Agent, or Firm* — Judy M. Mohr; McDermott Will & Emery LLP

(57) ABSTRACT

The biodegradable drug delivery systems described here are formulated for implantation into the nail unit and its surrounding tissues for the treatment of various nail unit conditions. The systems include non-temperature dependent phase change compositions that may be formulated as solutions, solids, semisolids, microparticles, or crystals.

21 Claims, No Drawings

(56) References Cited

FOREIGN PATENT DOCUMENTS

| | | |
|---|---|---|
| WO | WO 91/04058 A2 | 4/1991 |
| WO | WO 95/03775 A1 | 2/1995 |
| WO | WO 95/09590 A1 | 4/1995 |
| WO | WO 95/31178 A1 | 11/1995 |
| WO | WO 96/16643 A1 | 6/1996 |
| WO | WO 96/32107 A1 | 10/1996 |
| WO | WO 96/32419 A1 | 10/1996 |
| WO | WO 96/36317 A1 | 11/1996 |
| WO | WO 96/40072 A2 | 12/1996 |
| WO | WO 97/15282 A1 | 5/1997 |
| WO | WO 99/15210 A2 | 4/1999 |
| WO | WO 99/21908 A1 | 5/1999 |
| WO | WO 99/42147 A1 | 8/1999 |
| WO | WO 00/18821 A1 | 4/2000 |
| WO | WO 01/45742 A1 | 6/2001 |
| WO | WO 02/092661 A1 | 11/2002 |
| WO | WO 2004/000291 A1 | 12/2003 |
| WO | WO 2004/002456 A1 | 1/2004 |
| WO | WO 2004/060396 A2 | 7/2004 |
| WO | WO 2004/084826 A2 | 10/2004 |
| WO | WO 2006/063350 A2 | 6/2006 |
| WO | WO 2006/086888 A1 | 8/2006 |
| WO | WO 2007/139804 A1 | 12/2007 |
| WO | WO 2007/139804 A2 | 12/2007 |

OTHER PUBLICATIONS

Final Office Action mailed on Dec. 4, 2009 for U.S. Appl. No. 11/302,014, 13 pgs., filed Dec. 12, 2005.
Final Office Action mailed on Oct. 20, 2008, for U.S. Appl. No. 11/441,747, 12 pgs., filed May 25, 2006.
Final Office Action mailed on Jan. 22, 2010, for U.S. Appl. No. 11/441,747, 11 pgs., filed May 25, 2006.
Final Office Action mailed on Jul. 19, 2010, for U.S. Appl. No. 12/029,349, 10 pgs., filed Feb. 11, 2008.
International Preliminary Report on Patentability mailed on Dec. 11, 2008 for PCT Application No. PCT/US2007/012243, 9 pgs., filed on May 22, 2007.
International Search Report issued Aug. 7, 2006 for PCT Application No. PCT/US2005/044930, 4 pgs., filed Dec. 12, 2005.
International Search Report issued Nov. 30, 2007 for PCT Application No. PCT/US2007/012243, 5 pgs., filed May 22, 2007.
Karaca et al., "In Vitro Susceptibility Testing of Dermatophytes: Comparison of Disk Diffusion and Reference Broth Dilution Methods," Diagnostic Microbiology and Infectious Disease, vol. 48, pp. 259-264 (2004).
Lechenko, "Fungal Infections of the Skin. Contemporary Antimycoticks Before Dermatology," Comsilium Medicum, vol. 6, No. 3, 17 pgs. (2004) English machine translation included Located Online at <http:/www.medarena.ru/preparats/g-richter/includes/terbisil-st2.asp>.
Mashkovsky, "Drug Guide," vol. II, Moscow, Co. Ltd, pp. 156, 352-353,356,358-359,362,377-378, 25 pgs. (2001) Enqlish machine translation included.
Minghetti et al., "Dermal Patches for the Controlled Release of Miconazole: Influence of the Drug Concentration on the Technological Characteristics," Drug Development and Industrial Pharmacy, vol. 25, No. 5, pp. 679-684 (1999).
Non-Final Office Action mailed Dec. 10, 2007 for U.S. Appl. No. 11/302,014, 8 pgs., filed Dec. 12, 2005.
Non-Final Office Action mailed Apr. 9, 2008, for U.S. Appl. No. 11/441,747, 11 pgs., filed May,25, 2006.
Non-Final Office Action mailed on May 8, 2009, for U.S. Appl. No. 11/441,747, 15 pgs., filed May 25, 2006.
Non-Final Office Action mailed on Jul. 6, 2010, for U.S. Appl. No. 11/441,747, 11 pgs., filed May 25, 2006.
Non-Final Office Action mailed on Dec. 3, 2009 for U.S. Appl. No. 12/029,349, 13 pgs., filed Feb. 11, 2008.

\* cited by examiner

METHODS FOR TREATING CONDITIONS OF THE NAIL UNIT

CROSS-REFERENCE TO RELATED APPLICATIONS

This application is a divisional of U.S. application Ser. No. 12/985,996, filed Jan. 6, 2011, allowed, which is a continuation of U.S. application Ser. No. 11/441,747, filed May 25, 2006, abandoned, which is a continuation-in-part of U.S. application Ser. No. 11/302,014, filed Dec. 12, 2005, abandoned, which claims priority to U.S. Provisional Application No. 60/593,106, filed Dec. 10, 2004, each of which is hereby incorporated herein by reference its entirety.

FIELD

The compositions and methods described here are in the field of drug delivery. More specifically, the described compositions and methods relate to localized delivery of active agents to the nail unit and its surrounding tissues.

BACKGROUND

There are a variety of conditions that can affect the human nail. For example, the nail may be afflicted by inflammatory conditions such as psoriasis and lichen planus; nail tumors such as glomus tumor or digital myxoid cyst; and infections such as paronychia and onychomycosis. The pathophysiology of each condition is closely tied to nail structure and function. Thus, an understanding of nail anatomy and function is necessary in developing therapy for nail conditions.

In brief, the human nail is a modified cutaneous structure often described as a unit comprising several parts: the nail matrix, the nail bed, the nail plate, the nail folds, and the cuticle. The nail matrix is located beneath the proximal nail fold, and is the germinative portion of the nail unit that produces the nail plate. The nail bed is a layer of epithelium lying between the lunula (the portion of the nail matrix usually visible as a gray-white half moon projecting just distal to the proximal nail-fold cuticle) and the hyponychium (the distal epithelium at the free edge of the nail). The nail plate (fingernail or toenail) is produced by the matrix and progresses toward the tip of the fingers or toes as new plate is formed. The cutaneous tissue framing the nail unit, and which invaginates proximal and lateral to the nail plate, is referred to as the nail folds. The primary function of the nail plate is to protect the underlying digit, but fingernails and toenails are often also cosmetically important for many patients.

Nail infections are common conditions of the nail. Onychomycosis, a fungal infection of the nail bed, matrix, or nail plate, is the most common nail infection. The primary clinical features of onychomycosis are distal onycholysis (separation of the nail plate from the nail bed), subungual hyperkeratosis, and a dystrophic, discolored nail. Patients afflicted with onychomycosis are usually embarrassed by their nail disfigurement, but the infection is more than a cosmetic problem. It can sometimes limit mobility and indirectly decrease peripheral circulation, thereby worsening conditions such as venous stasis and diabetic ulcers. Fungal infections of the nail can also spread to other areas of the body and potentially to other persons. The fungal infection can be caused by dermatophytes (e.g., *Trichophyton rubrum* and *T. mentagrophytes*), but may also be due to infection by *Candida* species or non-dermatophyte molds such as *Aspergillus* species, *Scopulariosis brevicaulis*, *Fusarium* species, and *Scytalidium* species.

Currently, oral antifungal agents are the mainstay of treatment for onychomycosis. For example, ketoconazole, Sporonox® capsules (itraconazole) (Janssen Pharmaceutica Products, L.P., Titusville, N.J. and Ortho Biotech Products, L.P., Raritan, N.J.), Lamisil® tablets (terbinafine hydrochloride) (Novartis Pharmaceuticals, East Hanover, N.J.), Diflucan® tablets (fluconazole) (Pfizer, New York, N.Y.), and oral griseofulvin are commonly prescribed antifungal agents. However, these oral antifungal products are associated with many minor systemic side effects such as headaches, stomach upset, skin rashes, and photosensitivity, as well as serious systemic side effects such as heart failure and liver failure. Furthermore, fluconazole is not approved by the U.S. Food and Drug Administration (FDA) for the treatment of fungal nail infections. Moreover, although oral antifungal therapy is preferred, associated cure rates are not high and relapse is common. The prolonged treatment regimen of one dose daily for at least three months, or once weekly for nine to twelve months also leads to poor patient compliance with oral antifungal therapy.

Topical therapy with antifungal agents such as fluconazole, ketoconazole, miconazole, terbinafine, tolnaftate, and undecylenic alkanolamide is an alternative for patients in whom oral antifungal therapy is contraindicated. A topical solution, Penlac® nail laquer (ciclopirox solution, 8%) (Dermik Laboratories, Berwyn, Pa.), has also recently been approved by the FDA for the topical treatment of mild to moderate onychomycosis. However, the topical mode of administration is seldom effective to treat more than mild nail unit infections because the active agent is unable to effectively penetrate the nail. Topical therapy accompanied by chemical or physical abrasion of the nails has also been largely unsuccessful. Topical antifungal therapy usually also involves daily application to the nails for several months, and thus, also poses a compliance problem.

Other regimens for treating onychomycosis are described by Birnbaum et al. in U.S. Publication No. 2004/0062733 and Jackson et al. in U.S. Publication No. 2005/0042293. Specifically, in Birnbaum et al., the antifungal agent is placed under the fingernails by scraping them against a semi-solid, e.g., a bar of soap, or by injection of the agent under the nail plate through the hyponychium. In Jackson et al., a liquid or paste formulation of terbinafine is injected subcutaneously below the fungal infection. The liquid or paste then solidifies upon reaching body temperature. Jackson et al. describe their formulations as capable of delivering a high dose of drug over a short time period by using a lower drug load.

Accordingly, it would be desirable to have a drug delivery system for delivering antifungal agents and other active agents locally to the nail unit and its surrounding tissues for treatment of nail unit conditions. It would also be desirable to have a drug delivery system that can be precisely delivered to the portion of the nail unit that requires treatment. Similarly, it would be desirable to have drug delivery systems that simplify treatment regimens and improve patient compliance.

BRIEF SUMMARY

Described here are drug delivery systems and methods for treating conditions of the nail unit. The drug delivery systems include a therapeutically effective amount of a composition having an active agent for local sustained release useful for treating a nail unit condition. The compositions/drug delivery systems are usually configured for implantation in a nail unit and provide local sustained release of the active agent to treat conditions of the nail unit. The compositions/drug delivery systems are formulated such that they do not undergo a phase change with changes in temperature.

The drug delivery systems may be formulated as a solid, a liquid, a semisolid, microparticles, nanoparticles, or crystals. If a carrier is included, the choice of carrier will usually depend on such factors as the form of system, specific active agent used, and the intended duration of treatment. However, in all instances the carrier will be biocompatible. In one variation, the carrier is biodegradable. In another variation, the carrier is bioerodible. In yet another variation, the carrier is bioabsorbable.

Various active agents may be incorporated into the drug delivery systems, including, but not limited to, proteins, peptides, nucleic acids, small molecules, or other factors that stimulate nail or other tissue growth and regeneration, stimulate angiogenesis, enhance blood supply or circulation, and/ or modulate the immune system, reduce scarring, or improve healing. In one variation, antifungal agents, including, but not limited to, amorolfine; ciclopirox; flucytosine; griseofulvin; haloprogrin; potassium iodide sodium pyrithione; undecylenic acid; imidazole derivatives, including without limitation bifonazole, butoconazole, clotrimazole, econazole, ketoconazole, miconazole, oxiconazole, and sulconazole; triazoles, including without limitation itraconazole, fluconazole, and terconazole; allylamines, including without limitation naftifine and terbinafine, terbinafine FB; polyene antifungal antibiotics such as amphotericin B and nystatin; antifungal organic acids such as benzoic acid, salicylic acid, propionic acid, caprylic acid; and derivatives thereof may be used. In one variation, the antifungal agent may be combined with one or more additional antifungal agents. In another variation, the antifungal agent may be combined with one or more active agents from a different drug class. For example, the antifungal agent may be combined with one or more active agents including, but not limited to, an antibiotic agent, a steroidal anti-inflammatory agent, an analgesic, or an anesthetic.

The drug delivery systems may be used to treat various nail unit conditions. Examples of such nail unit conditions include, but are not limited to, medical conditions such as infections, inflammation, and tumors. Examples of nail infections include, but are not limited to, distal and lateral subungual onychomycosis, endonyx onychomycosis, white superficial onychomycosis, proximal subungual onychomycosis, total dystrophic onychomycosis, *Candida* onychomycosis, and paronychia. Examples of nail inflammation include, but are not limited to those conditions associated with inflammatory diseases such as psoriasis and lichen planus. Examples of nail tumors include, but are not limited to, glomus tumor, digital myxoid (mucus) cyst, subungual exostosis, and periungual angiofibromas. The drug delivery systems may also be used to treat cosmetic nail conditions such as pitting, brittleness, or discoloration. In one variation, the drug delivery systems may be used in combination with other conventional methods of treating nail unit conditions.

In general, the method for treating a nail unit condition includes administering locally within any portion of a digit, e.g., the distal portion, the proximal portion, and/or the middle portion, a composition having a therapeutically effective amount of an active agent. The drug delivery systems may be placed using a variety of methods, including, but not limited to, placement by forceps, placement through conduits such as trocars and needles, and placement using applicators configured to drive the system directly into the skin.

DETAILED DESCRIPTION

Described here are compositions and methods for treating conditions of the nail unit. The nail unit is located at the distal portion of the digits (i.e., tips of the fingers and toes). As used herein, the term "nail unit" refers to the nail matrix, nail plate, nail bed, nail folds, and cuticle, in combination, and the tissues adjacent to those structures in the distal phalanx. Examples of such adjacent tissues include epidermal tissue, dermal tissue, subcutaneous tissue (including adipose tissue), muscle, tendon, and bone in the region of the digit from the distal interphalangeal joint (or the distal-most interphalangeal joint) to the tip of the digit. As used herein, the term "nail unit condition" refers to a medical or cosmetic condition affecting any part of the nail unit. Furthermore, as used herein, the term "treat", "treating", or "treatment" refers to the resolution or reduction of symptoms or the underlying cause of the nail condition, prevention of a nail condition, or prevention of sequelae of a nail condition. The terms "nail" or "nail plate" are herein used interchangeably, and refer to fingernails or toenails.

The compositions may be of varying form. In one variation, the composition includes an active agent for the local treatment of a nail unit condition and a pharmaceutically acceptable carrier or matrix material. By "pharmaceutically acceptable" it is meant a substance that is biocompatible and can be administered to a patient without causing significant undesirable physiological effects, and a substance that does not interact in a significantly deleterious manner with any of the other components of the formulation in which it is contained. In another variation, the composition takes a pure crystalline form, and does not include a carrier or matrix material.

The compositions are also generally formulated for percutaneous delivery to the nail unit, and for sustained release of the active agent. They may be formulated to have drug loads of any amount. Once administered, the compositions release an active agent to treat a nail unit condition over time periods of less than one week, at least about one week, at least about two weeks, at least about four weeks, at least about eight weeks, or at least about twelve weeks or more.

Compositions.

As mentioned above, the compositions (drug delivery systems) described here may take varying forms, e.g., a solid, a semisolid, a solution, an emulsion, a non-temperature dependent phase change composition, microparticles, nanoparticles, crystals, and the like, depending on such factors as the particular active agent used, the type of nail condition being treated, and the medical history of the patient. However, in all instances, they are made to contain a drug load capable of delivering a therapeutically effective amount of an active agent to treat a nail unit condition. By "therapeutically effective amount" it is meant an amount of active agent effective to treat a nail unit condition. Furthermore, as used herein, the term "non-temperature dependent phase change composition" refers to a composition that does not undergo a phase transition, e.g., a transition between the solid, semi-solid, and liquid phases, due to a change in temperature.

The drug delivery systems described here may be delivered in any size, shape, and/or volume compatible with the site of implantation, as long as the systems have the desired drug loading and release kinetics, and deliver an amount of active agent that is therapeutic for the intended nail condition. For example, the solid drug delivery systems may be formed as particles, sheets, discs, filaments, rods, and the like. The solid systems may be formed to have volumes from between about 0 $mm^3$ to about 20 $mm^3$, between about 5.0 $mm^3$ to about 20 $mm^3$, between about 10 $mm^3$ to about 20 $mm^3$, or between about 15 $mm^3$ to about 20 $mm^3$. However, in one variation, the volume may be greater than 20 $mm^3$.

In one variation, the drug delivery system is formulated as a solid implant and includes active agent generally dispersed in a biocompatible carrier or matrix material (Examples 13-19). The carrier or matrix material may be any biocompatible polymeric or nonpolymeric material. The biocompatible materials may also be biodegradable, bioerodible, or bioabsorbable. As used herein, the term "biocompatible" refers to a carrier or matrix material that does not cause significant tissue irritation at the target site. The term "biodegradable" refers to carrier or matrix material that degrades over time by enzymatic or hydrolytic action, or other mechanism at the target site. By "bioerodible," it is meant that the carrier or matrix material erodes or degrades over time by contact with surrounding tissue fluids, through cellular activity or other physiological degradation mechanisms. By "bioabsorbable," it is meant that the carrier or matrix material breaks down and is absorbed by a cell, tissue, or other physiologic mechanism.

If a biocompatible polymer matrix is to be employed, selection of the matrix material will vary depending on the desired release kinetics, formulation constraints, the nature of the condition to be treated, and the like. Polymer characteristics that are considered include, but are not limited to, compatibility with the active agent of interest and processing temperatures. The biocompatible polymer matrix usually comprises less than about 70, less than about 65, less than about 60, less than about 55, less than about 50, less than about 45, less than about 40, less than about 35, less than about 30, less than about 25, less than about 20, less than about 10, less than about 15, less than about 10, less than about 5, less than about 2.5, or about zero weight percent of the drug delivery system. In one variation, the biocompatible polymer comprises about zero percent by weight of the drug delivery system. In another variation, the biocompatible polymer matrix comprises about 30% by weight of the drug delivery system.

Biocompatible polymer matrices which may be employed include, but are not limited to, poly(lactide)s; poly(glycolide)s; poly(lactide-co-glycolide)s; poly(lactic acid)s; poly(glycolic acid)s; poly(lactic acid-co-glycolic acid)s; poly(caprolactone)s; poly(orthoester)s; poly(phosphazene)s; poly(phosphoester)s; poly(hydroxybutyrate)s or copolymers including poly(hydroxybutyrate); poly(lactide-co-caprolactone)s; polycarbonates; polyesteramides; polyanhydrides; poly(dioxanone)s; poly(alkylene alkylate)s; copolymers of polyethylene glycol and a polyorthoester; biodegradable polyurethanes; poly(amino acid)s; polyetheresters; polyacetals; polycyanoacrylates; poly(oxyethylene)/poly(oxypropylene) copolymers; or blends, copolymers, and mixtures thereof.

In one variation, copolymers of glycolic and lactic acid are used. The percent of each monomer in poly(lactic-co-glycolic)acid (PLGA) copolymer may be 0-100%, about 15-85%, about 25-75%, or about 35-65%. If desired, a 50/50 PLGA copolymer may be employed. End-capped (e.g., acid-capped or ester-capped) or uncapped PLGA, or a combination of the two forms may also be used.

Other matrix forming materials that may be used alone or in combination with the biocompatible polymers mentioned above, include, but are not limited to, polyethylene glycol (PEG), vitamin E and its derivatives, dimethyl sulfone (MSM), carbamide, and blends and mixtures thereof. Natural polysaccharides such as chitosan, alginate, gelatin, and the like, may also be employed. Furthermore, extracellular matrix components such as collagen, laminin, hylauronic acid, and the like, may be used. In one variation, PEG is used as the matrix forming material. The amounts of these matrix forming materials incorporated in the drug delivery systems are usually the same as that described for biocompatible polymer matrices. In one variation, the drug delivery system comprises about 20% PEG as the matrix forming material.

In another variation, the solid drug delivery system may be formed by the following method. Two grams of Pharmacoat 606 (hydroxypropylmethylcellulose) (Shin-Etsu Chemical Co., Ltd., Tokyo, Japan) are wetted with 2.0 g of water. To that paste is added 3.0 g of microparticles made as described below, of the size fraction range of about 250 to about 300 microns. After thorough mixing, the resulting paste is then molded into a flat film of about 0.5 mm thickness using a carver press. The pressed film is then cut into about 1.0 mm$^2$, about 2.0 mm$^2$, or about 5.0 mm$^2$ discs using thin walled Teflon straws. Square-based columns can also be cut from the film of desired length and width by first trimming the pressed film and then cutting it to the desired width. The discs or square-based rod like systems are then dried overnight in a vacuum oven.

When the drug delivery system is formulated as microparticles, any one of the above-described polymers may be used. For example, PLGA may be employed. Large microparticles are usually prepared using a solvent evaporation process. In general, the solvent evaporation process involves emulsifying a polymer solution containing the drug in a second phase using a variety of different agitation techniques to create small droplets. The second or continuous phase consists of an emulsifier in a low volatility solvent that is also a poor solvent for the components of the first phase. During the evaporation of the highly volatile solvent off the first phase, the polymer and drug-containing droplets solidify. These formed microparticles are then separated by filtration from the continuous phase solvent and washed to remove remaining emulsifier.

Volume of the continuous phase, vessel and stirrer geometry, stir rate, concentration of emulsifier, volume and viscosity of the discontinuous phase, etc., are all important factors that influence the final particle size distribution, while the polymer depot material to drug ratio and the polymer depot chemistry define the biodegradation and agent release rate. Microparticle size may be tailored to the release profile or method of delivery desired.

When formulated as a semisolid, the drug delivery system will usually be a semisolid emulsion, a gel, or a paste. Semisolid emulsions are either oil-in-water or water-in-oil emulsions. Gels are typically suspension-type systems. Single phase gels contain gelling agents distributed substantially uniformly throughout the carrier liquid, which is typically aqueous, but which may also contain an alcohol and, optionally, an oil. Examples of gelling agents that may be used include, but are not limited to, crosslinked acrylic acid polymers such as the carbomer family of polymers, e.g., carboxypolyalkylenes that may be obtained commercially under the Carbopol™ trademark; hydrophilic polymers such as polyethylene oxides, polyoxyethylene-polyoxypropylene copolymers, and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof. Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Active Agents.

As used herein, the terms "active agent" and "drug" are used interchangeably and refer to any substance used to treat conditions of the nail. The active agents generally used in the drug delivery systems described here include, but are not limited to, analgesics (narcotic and non-narcotic analgesics), anesthetics, anti-infective agents, anti-inflammatory agents, chemotherapeutic agents, other small molecules, and combinations thereof. Anti-infective agents generally include antibacterial agents, antifungal agents, antiviral agents, and antiseptics. Examples of anti-inflammatory agents include nonsteroidal anti-inflammatory agents and steroidal anti-inflammatory agents. Examples of chemotherapeutic agents include alkaloids, alkylating agents, antineoplastic antibiotics, and antimetabolites. Nucleic acids, peptides, and proteins are other classes of active agents that may be used.

Examples of antifungal agents that may be incorporated into the drug delivery systems include amorolfine; ciclopirox; flucytosine; griseofulvin; haloprogrin; potassium iodide sodium pyrithione; undecylenic acid; imidazole derivatives, including without limitation bifonazole, butoconazole, clotrimazole, econazole, ketoconazole, miconazole, oxiconazole, and sulconazole; triazoles, including without limitation itraconazole, fluconazole, and terconazole; allylamines, including without limitation naftifine, terbinafine, and terbinafine FB; polyene antifungal antibiotics such as amphotericin B and nystatin; antifungal organic acids such as benzoic acid, salicylic acid, propionic acid, caprylic acid; and derivatives and combinations thereof.

The choice of a particular antifungal agent will be readily apparent to those skilled in the art. For example, dermatophyte onychomycosis may be treated by an antifungal agent effective against dermatophytes, such as terbinafine. As another example, a case of onychomycosis of uncertain fungal etiology may be treated with a broad-spectrum antifungal agent effective against dermatophytes, nondermatophyte molds, and yeasts, such as itraconazole.

The active agent may constitute from greater than about 30%, from greater than about 35%, from greater than about 40%, from greater than about 45%, from greater than about 50%, from greater than about 55%, from greater than about 60%, from greater than about 65%, from about 70%, from greater than about 75%, from greater than about 80%, from greater than about 85%, from greater than about 90%, from greater than about 95%, or about 100% by weight of the drug delivery system. In one variation, the active agent comprises greater than 100% of the drug delivery system. Drug loading may be varied to achieve high initial drug release (burst release). In one variation, the active agent comprises about 70% by weight of the drug delivery system.

The total dose delivered for an active agent will vary, depending on such factors as the type of nail unit condition being treated, the active agent used, and duration of therapy. The dosing regimen will also depend on factors such as the type of nail unit condition being treated, severity of the nail unit condition, and specific active agent used, but will usually involve delivery of the active agent in an amount capable of treating the nail unit condition over the intended duration of treatment. Thus, in the case of onychomycosis, the dosing regimen will generally be tailored so that tissue levels of the administered antifungal agent correlate to the minimal inhibitory concentration (MIC) for the suspected infecting agent (obtained by in vitro testing). For example, the MIC concentrations listed in Table 1 may be used in developing the dosing regimen (Karaca et al. *Diagnostic Microbiology and Infectious Disease* 48: 259-264 (2004), herein incorporated by reference in its entirety).

TABLE 1

Exemplary In Vitro MIC Concentrations for Select Fungal Species

| Anti-Fungal Agent | Fungal Species | MIC Ranges (mcg/ml) |
|---|---|---|
| Fluconazole | *Trichophyton rubrum* | <0.06->32 |
| | *Trichophyton mentagrophytes* | 16-32 |
| | *Trichophyton tonsurans* | 0.25-8 |
| | *Trichophyton verrucosum* | 16 |
| Ketoconazole | *Trichophyton rubrum* | <0.008->4 |
| | *Trichophyton mentagrophytes* | 0.008-4 |
| | *Trichophyton tonsurans* | 0.016-0.125 |
| | *Trichophyton verrucosum* | 4 |
| Itraconazole | *Trichophyton rubrum* | <0.001-1 |
| | *Trichophyton mentagrophytes* | 0.008-0.06 |
| | *Trichophyton tonsurans* | ≤0.001-0.5 |
| | *Trichophyton verrucosum* | 1 |
| Sulconazole | *Trichophyton rubrum* | <0.008-4 |
| | *Trichophyton mentagrophytes* | 0.016-0.125 |
| | *Trichophyton tonsurans* | ≤0.008-0.03 |
| | *Trichophyton verrucosum* | 4 |
| Oxiconazole | *Trichophyton rubrum* | <0.0008-2 |
| | *Trichophyton mentagrophytes* | 0.06-0.5 |
| | *Trichophyton tonsurans* | ≤0.0008-2 |
| | *Trichophyton verrucosum* | 4 |
| Bifonazole | *Trichophyton rubrum* | <0.016-1 |
| | *Trichophyton mentagrophytes* | 0.125-0.25 |
| | *Trichophyton tonsurans* | ≤0.016-0.5 |
| | *Trichophyton verrucosum* | 8 |
| Miconazole | *Trichophyton rubrum* | 0.008-4 |
| | *Trichophyton mentagrophytes* | 1 |
| | *Trichophyton tonsurans* | 0.016-0.25 |
| | *Trichophyton verrucosum* | 4 |
| Terbinafine | *Trichophyton rubrum* | ≤0.0001-1 |
| | *Trichophyton mentagrophytes* | ≤S0.001 |
| | *Trichophyton tonsurans* | ≤0.001-0.008 |
| | *Trichophyton verrucosum* | 1 |
| Griseofulvin | *Trichophyton rubrum* | 0.016-8 |
| | *Trichophyton mentagrophytes* | 0.016-0.125 |
| | *Trichophyton tonsurans* | 0.5-1 |
| | *Trichophyton verrucosum* | 1 |
| Ciclopiroxolamine | *Trichophyton rubrum* | <0.03-8 |
| | *Trichophyton mentagrophytes* | 0.5-1 |
| | *Trichophyton tonsurans* | 0.125-1 |
| | *Trichophyton verrucosum* | 4 |

Other substances may be included in the compositions for a variety of purposes. For example, buffering agents and preservatives may be employed. Preservatives which may be used include, but are not limited to, sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. Examples of buffering agents that may be employed include, but are not limited to, sodium carbonate, sodium borate, sodium phosphate, sodium acetate, sodium bicarbonate, and the like, as approved by the FDA for the desired route of administration. Electrolytes such as sodium chloride and potassium chloride may also be included in the compositions.

Administration.

One or more drug delivery systems may be inserted into the distal portion of a digit or into any portion of the nail unit by a variety of methods, including placement using forceps, conduits such as trocars and needles, and applicators configured to drive the system directly into the skin. The conduit may be configured to be malleable. If desired, the conduit, e.g., a needle, may also be adapted so that a portion of it can remain at the target site after injection. For example, the distal end of the needle may be configured such that it can separate from the rest of the needle.

The conduit or applicator may be preloaded with one or more drug delivery systems. In one variation, the drug delivery system(s) may reside within a conduit lumen. In another variation, the drug delivery system(s) may be incorporated on the tip of a sharp-tipped applicator or provided in a cartridge to be used with an applicator, e.g., a spring powered applicator.

In one variation, the method of implantation generally first involves accessing the target area within the distal portion of the digit with the conduit. Once within the target area, e.g., the germinal matrix, a push rod, pressurized gas, or jet injection may be used to push the drug delivery system out of the conduit into the target area. In general, the drug delivery system is placed in or in close proximity to the area affected by the nail condition. Thus, if onychomycosis is the nail condition being treated, the drug delivery system is usually placed at or in close proximity to the germinal matrix to allow uptake of the active agent into the growing nail. Similarly, if paronychia is the nail condition being treated, the drug delivery system is usually placed at or in close proximity to the proximal nail fold. After delivery to the target area, the drug delivery systems do not undergo a phase change due to changes in temperature, e.g., upon reaching body temperature.

Although the drug delivery systems have been described as being placed within the nail unit or within the distal portion of a digit, the method of administration is not so limited. If desired, the drug delivery systems may be placed within the tissue of any part of a digit to treat conditions affecting those parts. For example, they may be placed within a middle portion of a digit and/or a proximal portion of a digit. The middle portion of a digit generally refers to those tissues or structures surrounding the middle phalanx (second phalanx). The proximal portion of a digit generally refers to those tissues or structures surrounding the proximal phalanx (first phalanx) and/or a metacarpal bone.

Applications.

Examples of nail unit conditions that may be treated with the described drug delivery systems include, but are not limited to, medical conditions such as infections, inflammation, and tumors. Examples of nail infections include, but are not limited to, distal and lateral subungual onychomycosis, endonyx onychomycosis, white superficial onychomycosis, proximal subungual onychomycosis, total dystrophic onychomycosis, *Candida* onychomycosis, and paronychia. Examples of nail inflammation include, but are not limited to those conditions associated with inflammatory diseases such as psoriasis and lichen planus. Examples of nail tumors include, but are not limited to, glomus tumor, digital myxoid (mucus) cyst, subungual exostosis, and periungual angiofibromas. The drug delivery systems may also be used to treat cosmetic nail unit conditions such as pitting, brittleness, or discoloration.

EXAMPLES

The following examples serve to more fully describe the manner of making and using the above-described compositions. It is understood that these examples in no way serve to limit the scope of this invention, but rather are presented for illustrative purposes.

Unless otherwise indicated, the substances used in the examples were obtained from the sources listed below:
Aldrich Chemicals, Milwaukee, Wis.
Vancomycin
Dow Chemical, Midland, Mich.
HPMC
PEG 3350
Eastman Chemicals, Llangefni, Anglesey, UK
Vitamin E TPGS
EMD Chemicals, Darmstadt, Germany
EDTA
Fluka, Allentown, Pa.
Ciprofloxacin
JT Baker, Philipsburg, N.J.
Carbamide
Lakeshore Biomaterials, Birmingham, Ala.
PLGA
Norland High Molecular Weight Fish Gelatin, Cranbury, N.J.
Gelatin
Recordati Espana S.LI, Beniel (Murcia)
Fluconazole
Itraconazole
Recordati S.p.A., Milano, Italy
Terbinafine
Sigma-Aldrich, Saint Louis, Mo.
Dexamethasone
Ketorolac
Lidocaine
Poly(vinyl alcohol)
Spectrum Chemical Mfr., Gardena, Calif.
Vitamin E succinate Furthermore, the following examples will employ, unless otherwise indicated, conventional techniques of pharmaceutical formulation, medicinal chemistry, and the like, which are within the skill of the art. Such techniques are explained fully in the literature. Efforts have been made to ensure accuracy with respect to numbers (e.g., amounts, temperature, etc.), but some experimental error and deviation should be accounted for. Unless indicated otherwise, parts are parts by weight, temperature is in degrees Celsius (° C.) and pressure is at or near atmospheric pressure at sea level. All components are obtainable commercially unless otherwise indicated.

Example 1

Preparation of Terbinafine Microparticles and In Vitro Release of Terbinafine

A predetermined amount of the drug terbinafine HCl (3.3 g) is added to the oil phase (polymer in solvent 5.0 g/7.0 g). The polymer is 50/50 polylactic acid/glycolic acid with a molecular weight of about 40,000 g/mol, and the solvent is methylene chloride. The aqueous phase (23.5 g) contains the emulsifier polyvinyl alcohol (2.5 g) to adjust viscosity. Approximately three drops of octanol is added to the aqueous phase to prevent or minimize foaming. Furthermore, to prevent drug loss into the aqueous phase, the aqueous phase is saturated with the drug.

Next, a one inch impeller mixer is used to agitate the continuous phase at about 600 rpm. The oil phase is then slowly added to the aqueous phase. This mixture is stirred for about an hour, and air passed over it to remove the evaporating solvent. After ten minutes, the stirrer speed is reduced to 400 rpm. At about 30 minutes, most of the methylene chloride will have evaporated and the emulsion droplets solidified. Agitation is continued at about 60 rpm for another 45 minutes to prevent agglomeration. The solidified microparticles are then separated from the aqueous solution using a vacuum funnel and filter paper. After continued washing to remove any emulsifier, the microparticles are dried and sieved. Only particles smaller than 400 microns are kept. By adjusting the continuous phase stirring speed, the yield in different particle size classes can be adjusted.

Terbinafine release from the microparticles can then be measured as follows. Large terbinafine microparticles of about 330 micron radius made according to the method described above are placed into screw cap glass vials filled with 10 ml of phosphate buffered saline (PBS) and placed into a shaking water bath kept at a temperature of 35° C. After centrifuging, samples of 1.0 ml are removed at designated time points and replaced with the same amount of fresh PBS. The samples are then analyzed for drug concentration by techniques known in the art, such as spectroscopy, HPLC, mass spectroscopy, and the like. These microparticles are expected to have a drug release profile as shown in the following table:

|  | Time | | | |
| --- | --- | --- | --- | --- |
|  | Day 2 | Day 14 | Day 30 | Day 60 |
| % release | 10-15 | 30-35 | 70-75 | 90-95 |

The microparticles generally provide high initial drug release (burst release). This is desirable, for example, to load up the tissue quickly and prevent shedding of conidia in the early days of injection. Subsequent drug release would be fashioned to be at a lower rate, but would be sufficient to maintain the appropriate minimum inhibitory concentration (MIC) and/or minimal fungicidal concentration (MFC) of the antifungal agent.

Example 2

Itraconazole Microparticles and In Vitro Release of Itraconazole

Microparticles including itraconazole are prepared according to the method described in Example 1 at a size of about 400 microns. In vitro drug release is measured in the same manner as Example 1. These microparticles are expected to have a drug release profile as shown in the following table:

| | Time | | | |
|---|---|---|---|---|
| | Day 2 | Day 14 | Day 30 | Day 45 |
| % release | 20-25 | 60-65 | 80-85 | 95-100 |

Example 3

Ciprofloxacin Microparticles and In Vitro Release of Ciprofloxacin

Microparticles are prepared as described in Example 1, except that ciprofloxacin is added instead of terbinafine. The size of the microparticles should be about 250 microns. These microparticles are expected to have a drug release profile as shown in the following table:

| | Time | | | |
|---|---|---|---|---|
| | Day 1 | Day 2 | Day 14 | Day 30 |
| % release | 20-25 | 30-35 | 70-75 | 90-95 |

These microparticles provide a high initial burst of active agent, which would, in the clinical environment, generate locally high anti-infective concentration levels. This is desirable, for example, after surgery, to prevent microorganisms that may be introduced during the surgical procedure from replicating and causing an infection of the wound area. Subsequent drug release would be lower, but sufficient to generate an in vivo maintenance level that can prevent the microbial re-colonization of the surgical area. At day 7, it is believed that the cumulative drug release will equal the theoretical drug-loading amount.

Example 4

Terbinafine Solid Drug Delivery Systems

Preparation of a terbinafine drug delivery system may be accomplished by wetting 2.0 g of Metolose SR (90SH, 100000SR, methylcellulose, Shin-Etsu Chemical Co., Ltd., Tokyo) with 2.0 g of water. To that paste is added 4.5 g of terbinafine. After thorough mixing, the resulting paste is then molded into a flat film of about 0.4 mm thickness using a carver press. The pressed film is then cut into about 1.0 $mm^2$, about 2.0 $mm^2$, or about 5.0 $mm^2$ discs using thin walled Teflon straws. Square-based columns can also be cut from the film of desired length and width by first trimming the pressed film and then cutting it to the desired width. The discs or square-based rod like systems are then dried overnight in a vacuum oven.

In another variation, the terbinafine drug delivery system may be formed as a strip. A saturated solution of gelatin in water is prepared. Micronized terbinafine is added to achieve a mixture having a polymer to drug ratio of 30:70. The resulting mixture is poured onto a glass plate covered with a standard silicone coated polyester release liner. A gardener knife is used to create about a 300 mm thick film. The glass plate with the resulting film is placed into a vacuum oven and dried overnight at 80° C. The resulting film is then cut into strips of desired length and width.

Example 5

Vancomycin Solid Drug Delivery Systems

Vancomycin drug delivery systems may be made by wetting 2.0 g of Metolose SR with 2.0 grams of water. To that paste is added 3.6 g of vancomycin. After thorough mixing, the resulting paste is then molded into a flat film of about 1.0 mm thickness using a carver press. The pressed film is then cut into about 1.0 $mm^2$, about 2.0 $mm^2$, or about 5.0 $mm^2$ discs using thin walled Teflon straws. Square-based columns can also be cut from the film of desired length and width by first trimming the pressed film and then cutting it to the desired width. The discs or square-based rod like systems are then dried overnight in a vacuum oven.

In another variation, the vancomycin drug delivery systems are made by wetting 2.0 g of L-HPC (LH-20, low-substituted hydroxypropylcellulose) (Shin-Etsu Chemical Co., Ltd., Tokyo, Japan) with 2.0 g of water. To that paste is added 3.6 g of vancomycin. After thorough mixing, the resulting paste is then molded into a flat film of about 1.0 mm thickness using a carver press. The pressed film is then cut into about 1.0 mm², about 2.0 mm², or about 5.0 mm² discs using thin walled Teflon straws. Square-based columns can also be cut from the film of desired length and width by first trimming the pressed film and then cutting it to the desired width. The discs or square-based rod like systems are then dried overnight in a vacuum oven.

Example 6

Itraconazole Solid Drug Delivery System

Itraconazole drug delivery systems may be made by wetting 2.0 g of Metolose SR with 2.0 g of water. To that paste is added 4.0 g of itraconazole. After thorough mixing, the resulting paste is then molded into a flat film of about 1.0 mm thickness using a carver press. The pressed film is then cut into about 1.0 mm², about 2.0 mm², or about 5.0 mm² discs using thin walled Teflon straws. Square-based columns can also be cut from the film of desired length and width by first trimming the pressed film and then cutting it to the desired width. The discs or square-based rod like systems are then dried overnight in a vacuum oven.

Example 7

Dexamethasone Solid Drug Delivery System

Dexamethasone drug delivery systems may be formed by wetting 2.0 g of L-HPC 2.0 g of water. To that paste is added 4.0 g of dexamethasone. After thorough mixing, the resulting paste is then molded into a flat film of about 1.0 mm thickness using a carver press. The pressed film is then cut into about 1.0 mm², about 2.0 mm², or about 5.0 mm² discs using thin walled Teflon straws. Square-based columns can also be cut from the film of desired length and width by first trimming the pressed film and then cutting it to the desired width. The discs or square-based rod like systems are then dried overnight in a vacuum oven.

Example 8

Lidocaine Solid Drug Delivery System

Lidocaine drug delivery systems may be made by wetting 2.0 g of Metolose SR with 2.0 g of water. To that paste is added 2.0 g of lidocaine. After thorough mixing, the resulting paste is then molded into a flat film of about 1.0 mm thickness using a carver press. The pressed film is then sprayed on one side with a solution of 0.5 wt % CA-398-10NF solution in acetone. Strips of about 3.0 mm by about 5.0 mm are then cut and dried overnight in a vacuum oven.

Example 9

Ketorolac Solid Drug Delivery System

Ketorolac drug delivery systems may be formed by first preparing a saturated solution of hyaluronic acid in water. Micronized S(−)ketorolac is then added to the solution to achieve a mixture having a polymer to drug ratio of 40:60. The resulting mixture is poured onto a glass plate covered with a standard silicone coated polyester release liner. A gardener knife is used to spread the mixture and create about a 300 mm thick film. The glass plate with the resulting film is placed into a vacuum oven and dried overnight at 80° C. The resulting film is then cut into strips of desired length and width.

Example 10

Methadone Solid Drug Delivery System

Methadone drug delivery systems may be formed by first preparing a saturated solution of hyaluronic acid in water. Micronized R(−)methadone is then added to the solution to achieve a mixture having a polymer to drug ratio of 40:60. The resulting mixture is poured onto a glass plate covered with a standard silicone coated polyester release liner. A gardener knife is used to spread and create about a 300 mm thick film. The glass plate with the resulting film is placed into a vacuum oven and dried overnight at 80° C. The resulting film is then cut into strips of desired length and width.

Example 11

Combination Dexamethasone and Itraconazole Drug Delivery Systems

Combination dexamethasone and itraconazole drug delivery systems may be made by wetting 2.0 g of AQOAT Enteric Coating Agent (AS/HF, hydroxypropylmethyl cellulose acetate succinate) (Shin-Etsu Chemical Co., Ltd., Tokyo, Japan) with 2 g of water. To that paste is added 1.5 g of dexamethasone and 3.5 g of itraconazole. After thorough mixing, the resulting paste is then molded into a flat film of about 1.0 mm thickness using a carver press. The pressed film is then cut into about 1.0 mm², about 2.0 mm², or about 5.0 mm² discs using thin walled Teflon straws. Square-based columns can also be cut from the film of desired length and width by first trimming the pressed film and then cutting it to the desired width. The discs or square-based rod like systems are then dried overnight in a vacuum oven.

In another variation, the combination dexamethasone and itraconazole drug delivery systems may be made by wetting 2.0 g of gelatin with 2.0 g of water. To that paste is added 1.5 g of dexamethasone and 3.0 g of itraconazole. After thorough mixing, the resulting paste is then molded into a flat film of about 1.0 mm thickness using a carver press. The pressed film is then cut into about 1.0 mm², about 2.0 mm², or about 5.0 mm² discs using thin walled Teflon straws. Square-based columns can also be cut from the film of desired length and width by first trimming the pressed film and then cutting to the desired width. The discs or square-based rod like systems are then dried overnight in a vacuum oven.

Example 12

Combination Dexamethasone and Ciprofloxacin Drug Delivery System

Combination dexamethasone and ciprofloxacin drug delivery systems may be formed by wetting 2.0 g of gelatin with 2.0 g of water. To that paste is added 1.5 grams dexamethasone and 1.5 g of ciprofloxacin. After thorough mixing, the resulting paste is then molded into a flat film of about 1.0 mm thickness using a carver press. The pressed film is then cut into about 1.0 mm², about 2.0 mm², or about 5.0 mm² discs using thin walled Teflon straws. Square-based columns can also be cut from the film of desired length and width by first trimming the pressed film and then cutting to the desired width. The discs or square-based rod like systems are then dried overnight in a vacuum oven.

Example 13

Dexamethasone Extruded Drug Delivery System

One gram of a well-mixed powder of dexamethasone and 50/50 polylactic acid/polyglycolic acid copolymer with an inherent viscosity of 0.24 was measured and filled into a batch extruder and heated for one hour at 95° C. The melt was then extruded through a circular orifice to create a filament having a diameter of about 0.4 mm. From the filament, various length subunits were cut and tested for in vitro drug release using the USP Paddle apparatus, in PBS, pH 7.4. Dexamethasone release from a 2.2 mm long filament extruded through a 400 um circular orifice is shown in the following table:

|           | Time  |       |        |        |
|-----------|-------|-------|--------|--------|
|           | Day 1 | Day 2 | Day 14 | Day 30 |
| % release | 19    | 30    | 69     | 89     |

Example 14

Terbinafine Extruded Drug Delivery Systems—70% Terbinafine Loading

PEG Matrix.

The terbinafine extruded delivery system was made by first mixing terbinafine HCl and PEG at a ratio of 70:30 respectively (total weight of the mixture was 0.5 g). The mixture was filled into a batch extruder and heated for one hour at 115° C. The melt was then extruded through a circular orifice to create a filament having a diameter of about 0.4 mm. From the filament, various length subunits were cut and tested for in vitro drug release, as described in Example 1, except that instead of removing 1.0 ml per sample, 8.0 ml was removed per sample. Sample pH measured 7.4. Terbinafine release from a 3.0 mm long filament is shown in the following table:

|           | Time  |       |        |        |
|-----------|-------|-------|--------|--------|
|           | Day 1 | Day 2 | Day 14 | Day 30 |
| % release | 4     | 91    | 100    | 100    |

PEG/Vitamin E TPGS Matrix.

The terbinafine extruded delivery system was made by first preparing a well-mixed powder containing terbinafine HCl, PEG 3350, and D-α-tocopheryl polyethylene glycol 1000 succinate (vitamin E TPGS) at a ratio of 70:15:15, respectively (total weight of the mixture was 0.25 g). The well-mixed powder was filled into a batch extruder and heated for 1 hour at 115° C. The melt was then extruded through a circular orifice to create a filament having a diameter of about 330 um. From the filament, various length subunits were cut and tested for in vitro drug release, as described in Example 1. As above, the receptor medium was PBS and the volume removed per sample was 8 ml. The pH of the samples was 7.4. Terbinafine release from a 3.0 mm long filament is shown in the following table.

|           | Time  |       |        |        |
|-----------|-------|-------|--------|--------|
|           | Day 1 | Day 2 | Day 14 | Day 30 |
| % release | 18    | 22    | 37     | 50     |

PEG/PLGA Matrix.

The terbinafine extruded delivery system was made by first preparing a mixture of terbinafine HCl, PEG, and PLGA at a ratio of 70:15:15, respectively (total weight of the mixture was 0.25 g). The well-mixed powder was filled into a batch extruder and heated for 1 hour at 115° C. The melt was then extruded through a circular orifice to create a filament having a diameter of about 330 um. From the filament, various length subunits were cut and tested for in vitro drug release, as described in Example 1. As above, the receptor medium was PBS and the volume removed per sample was 8 ml. The pH of the samples was 7.4. Terbinafine release from a 3.0 mm long filament is shown in the following table:

|           | Time  |       |        |        |
|-----------|-------|-------|--------|--------|
|           | Day 1 | Day 2 | Day 14 | Day 30 |
| % release | 4     | 7     | 32     | 52     |

In yet another variation, the terbinafine extruded delivery system was made by first preparing a mixture of terbinafine HCl, PLGA, and PEG at a ratio of 70:20:10 (total weight of the mixture was 0.25 g). The well-mixed powder was filled into a batch extruder and heated for 1 hour at 115° C. The melt was then extruded through a circular orifice to create a filament having a diameter of about 415 um. From the filament, various length subunits were cut and tested for in vitro drug release, as described in Example 1. As above, the receptor medium was PBS and the volume removed per sample was 8 ml. The pH of the samples was 7.4. Terbinafine release from a 3.0 mm long filament is shown in the following table:

|           | Time  |       |        |        |
|-----------|-------|-------|--------|--------|
|           | Day 1 | Day 2 | Day 14 | Day 30 |
| % release | 1     | 3     | 11     | 22     |

PLGA/Vitamin E Succinate Matrix.

The terbinafine extruded delivery system was made by first preparing a mixture of terbinafine HCl, PLGA, and vitamin E succinate at a ratio of 70:27.5:2.5, respectively (total weight of the mixture was 0.25 g). The well-mixed powder was filled into a batch extruder and heated for 1 hour at 115° C. The melt was then extruded through a circular orifice to create a filament having a diameter of about 415 um. From the filament, various length subunits were cut and tested for in vitro drug release, as described in Example 1. As above, the receptor medium was PBS and the volume removed per sample was 8 ml. The pH of the samples was 7.4. Terbinafine release from a 3.0 mm long filament is shown in the following table:

| | Time | | | |
|---|---|---|---|---|
| | Day 1 | Day 2 | Day 14 | Day 30 |
| % release | 1 | 3 | 5 | 15 |

Vitamin E Succinate/PEG 3350 Matrix.

The terbinafine extruded delivery system was made by first preparing a mixture of terbinafine HCl, vitamin E succinate, and PEG 3350 at a ratio of 70:15:15, respectively (total weight of the mixture was 0.25 g). The well-mixed powder was filled into a batch extruder and heated for 1 hour at 115° C. The melt was then extruded through a circular orifice to create a filament having a diameter of about 415 um. From the filament, various length subunits were cut and tested for in vitro drug release, as described in Example 1. As above, the receptor medium was PBS and the volume removed per sample was 8 ml. The pH of the samples was 7.4. Terbinafine release from a 3.0 mm long filament is shown in the following table:

| | Time | | | |
|---|---|---|---|---|
| | Day 1 | Day 2 | Day 14 | Day 30 |
| % release | 16 | 22 | 100 | 100 |

PLGA/Dimethyl Sulfone Matrix.

The terbinafine extruded delivery system was made by first preparing a mixture of terbinafine HCl, PLGA, and dimethyl sulfone at a ratio of 70:25:5, respectively (total weight of the mixture was 0.25 g). The well-mixed powder was filled into a batch extruder and heated for 1 hour at 115° C. The melt was then extruded through a circular orifice to create a filament having a diameter of about 415 um. From the filament, various length subunits were cut and tested for in vitro drug release, as described in Example 1. As above, the receptor medium was PBS and the volume removed per sample was 8 ml. The pH of the samples was 7.4. Terbinafine release from a 3.0 mm long filament is shown in the following table:

| | Time | | | |
|---|---|---|---|---|
| | Day 1 | Day 2 | Day 14 | Day 30 |
| % release | 1 | 2 | 8 | 15 |

Carbamide Matrix.

The terbinafine extruded delivery system was made by first preparing a mixture of terbinafine HCl and carbamide at a ratio of 70:30, respectively (total weight of the mixture was 0.25 g). The well-mixed powder was filled into a batch extruder and heated for 1 hour at 115° C. The melt was then extruded through a circular orifice to create a filament having a diameter of about 415 um. From the filament, various length subunits were cut and tested for in vitro drug release, as described in Example 1. As above, the receptor medium was PBS and the volume removed per sample was 8 ml. The pH of the samples was 7.4. Terbinafine release from a 3.0 mm long filament is shown in the following table:

| | Time | | | |
|---|---|---|---|---|
| | Day 1 | Day 2 | Day 14 | Day 30 |
| % release | 1 | 2 | 11 | 19 |

Example 15

Terbinafine Extruded Drug Delivery System—80% Terbinafine Loading

The terbinafine extruded delivery system was made by first mixing terbinafine HCl and PEG as the matrix-forming material at a ratio of 80:20 respectively (total weight of the mixture is 0.5 g). The mixture was filled into a batch extruder and heated for one hour at 115° C. The melt was then extruded through a circular orifice to create a filament having a diameter of about 0.4 mm. From the filament, various length subunits were cut and tested for in vitro drug release, as described in Example 1, except that instead of removing 1.0 ml per sample, 8.0 ml was removed per sample. Sample pH measured 7.4. Terbinafine release from a 3.0 mm long filament is shown in the following table:

| | Time | | | |
|---|---|---|---|---|
| | Day 1 | Day 2 | Day 14 | Day 30 |
| % release | 38 | 100 | 100 | 100 |

Example 16

Fluconazole Extruded Drug Delivery Systems—80% Fluconazole Loading

The fluconazole extruded delivery system was made by first mixing fluconazole and PEG as the matrix-forming material at a ratio of 80:20 respectively (total weight of the mixture is 0.5 g). The mixture was filled into a batch extruder and heated for one hour at 115° C. The melt was then extruded through a circular orifice to create a filament having a diameter of about 0.4 mm. From the filament, various length subunits were cut and tested for in vitro drug release, as described in Example 1, except that instead of removing 1.0 ml per sample, 8.0 ml was removed per sample. Sample pH measured 7.4. Terbinafine release from a 3.0 mm long filament is shown in the following table:

| | Time | | | |
|---|---|---|---|---|
| | Day 1 | Day 2 | Day 14 | Day 30 |
| % release | 60 | 100 | 100 | 100 |

Example 17

Itraconazole Extruded Drug Delivery System

The itraconazole extruded delivery system was made by first mixing itraconazole and PEG as the matrix-forming material at a ratio of 80:20 respectively (total weight of the mixture is 0.5 g). The mixture was filled into a batch extruder and heated for one hour at 115° C. The melt was then extruded through a circular orifice to create a filament having a diameter of about 0.4 mm. From the filament, various length subunits were cut and tested for in vitro drug release, as described in Example 1, except that instead of removing 1.0 ml per sample, 8.0 ml was removed per sample. Sample pH measured 7.4. Terbinafine release from a 3.0 mm long filament is shown in the following table:

|  | Time | | | |
| --- | --- | --- | --- | --- |
|  | Day 1 | Day 2 | Day 14 | Day 30 |
| % release | 30 | 100 | 100 | 100 |

Example 18

Ketorolac Extruded Drug Delivery System

One gram of well-mixed powder containing the active agent S(−)ketorolac and 50/50 polylactic acid/polyglycolic acid copolymer with an average molecular weight of 20,000 g/mol at a ratio of 50:50 is first prepared. The well-mixed powder is then filled into a batch extruder and heated for 1 hour at 115° C. The melt is extruded through a circular orifice to create a filament having a diameter of about 0.33 mm. Subunits of various lengths may then be cut from the filament.

Example 19

Methadone Extruded Drug Delivery System

Methadone extruded drug delivery systems may be made by first mixing R(−) methadone with a 50/50 polylactic acid/polyglycolic acid copolymer with an average molecular weight of 45,000 g/mol at a ratio of 60:40, respectively (total weight of the mixture is 0.5 g). The well-mixed powder is filled into a batch extruder and heated for 1 hour at 115° C. The melt is then extruded through a circular orifice to create a filament having a diameter of about 0.9 mm. Subunits of various lengths may then be cut from the filament.

Example 20

Clindamycin Extruded Drug Delivery System

Clindamycin extruded drug delivery systems may be made by mixing clindamycin and a 50/50 polylactic acid/polyglycolic acid copolymer with an average molecular weight of 20,000 g/mol at a ratio of 50:50 (total weight of the mixture is 0.5 g). The well-mixed powder is filled into a batch extruder and heated for 1 hour at 115° C. The melt is then extruded through a circular orifice to create a filament having a diameter of about 0.5 mm diameter. Subunits of various lengths may then be cut from the filament.

Example 21

Gancyclovir Extruded Drug Delivery System

One gram of well-mixed powder of ganciclovir and a 50/50 polylactic acid/polyglycolic acid copolymer with an average molecular weight of 50,000 g/mol at a ratio of 80:20, respectively, is prepared. The well-mixed powder is filled into a batch extruder and heated for 1 hour at 110° C. The melt is then extruded through a circular orifice to create a filament having a diameter of about 1.1 mm. The extruded filament sections are dipped into a 3-wt % aqueous solution of Pharmacoat 615. The coated filament sections are then dried overnight in a vacuum oven at room temperature. Subunits of various lengths may then be cut from the overcoated filament.

Example 22

Combination Dexamethasone and Vitamin E Extruded Drug Delivery Systems

Combination dexamethasone and vitamin E extruded drug delivery systems may be made by mixing the vitamin E ester d-α-tocopheryl acetate with dexamethasone powder in a ratio of 50:50 and then extruding the mixture through a round orifice having a diameter of about 0.5 mm at a temperature of 50° C. The melt is then sub-divided into dosage units of various lengths and cooled overnight.

In another variation, the vitamin E ester d-α-tocopheryl succinate is mixed with dexamethasone powder in a ratio of 50:50 and then extruded through a round orifice having a diameter of about 0.5 mm at a temperature of 90° C. The melt is then sub-divided into dosage units of various lengths and cooled overnight.

Example 23

Terbinafine Liquid Drug Delivery System

Carbamide and Terbinafine were mixed at ratios of 70:30, 60:40, 50:50, 40:60, and 30:70, respectively, and then heated in small HPLC glass vials up to 170° C. The resulting liquid was tested for injection feasibility. Tests were conducted to explore the physical properties of the solution as a function of temperature.

Example 24

Free-Base Terbinafine

An aqueous solution of terbinafine HCl may be reacted with sodium hydroxide at a pH of 7.5 to 13.0 to form the freebase (base) form of the drug. The free base form is to form an oily solution that can be delivered to the site in this form. A mixture of the free base and the salt may also be employed.

Example 25

Terbinafine Microparticles—Less than 30% Terbinafine Loading and In Vitro Release of Terbinafine Microparticles including terbinafine are prepared according to the method described in Example 1. In order to decrease the size of the average microparticle to about 50-100 um, the stirrer speed may be adjusted to a higher rpm, for example, 1250-1500 rpm. These smaller sized microparticles are expected to have a better penetration profile if the method of administration involves pushing the microparticles into and/ or through the skin, e.g., by using a push rod, pressurized gas, jet injection, and the like. Additionally, to increase the duration of drug release, a polymer of higher molecular weight, for example, 75,000 g/mol, may be used. To further control drug release the load in the microparticle may be dropped by using a smaller drug to polymer ratio (e.g., 1.5 g drug/5 g polymer). In vitro drug release may then be measured in the same manner as Example 1. These microparticles are expected to have a drug release profile as shown in the following table:

|  | Time | | | |
| --- | --- | --- | --- | --- |
|  | Day 1 | Day 21 | Day 45 | Day 70 |
| % release | 20-25 | 50-55 | 80-85 | 95-100 |

All publications, patents, and patent applications cited herein are hereby incorporated by reference in their entirety for all purposes to the same extent as if each individual publication, patent, or patent application were specifically and individually indicated to be so incorporated by reference. Although the foregoing compositions and methods have been described in some detail by way of illustration and example for purposes of clarity of understanding, it will be readily apparent to those of ordinary skill in the art in light of this description that certain changes and modifications may be made thereto without departing from the spirit and scope of the appended claims.

It is claimed:

1. A method for treating a nail unit condition, comprising: administering to a nail unit of a digit an solid implant comprised of a bioerodible, non-temperature dependent phase change polymer and a therapeutically effective amount of an antifungal agent, wherein the solid implant has a volume greater than 0 mm$^3$ to about 20 mm$^3$ and is sized and shaped for implantation into a nail unit and is configured to release the active agent over a period of at least two weeks.

2. The method of claim 1, wherein the nail unit condition is a fungal infection.

3. The method of claim 2, wherein the fungal infection is onychomycosis.

4. The method of claim 1, wherein the digit comprises a nail unit having a matrix, and the implant is administered within the matrix.

5. The method of claim 4, wherein the digit comprises a nail unit having a nail fold, and the implant is administered within the nail fold.

6. The method of claim 1, wherein the digit is a finger.

7. The method of claim 1, wherein the digit is a toe.

8. The method of claim 1, wherein the implant is administered by injection through a conduit.

9. The method of claim 8, wherein the conduit comprises a needle.

10. The method of claim 9, wherein a portion of the needle is configured to remain in the digit after injection of the implant.

11. The method of claim 1, wherein an applicator is used to administer the implant to the digit.

12. The method of claim 1, wherein the implant comprises microparticles.

13. The method of claim 1, wherein the implant is formulated as a semi-solid.

14. The method of claim 13, wherein the semi-solid is a gel or paste.

15. The method of claim 1, wherein the implant comprises the active agent in crystalline form.

16. The method of claim 1, wherein the antifungal agent is selected from the group consisting of amorolfine, ciclopirox, flucytosine, griseofulvin, haloprogrin, potassium iodide sodium pyrithione, undecylenic acid, imidazole derivatives, triazole derivatives, allylamines, polyene antifungal antibiotics, antifungal organic acids, and combinations thereof.

17. The method of claim 16, wherein the imidazole derivative is selected from the group consisting of bifonazole, butoconazole, clotrimazole, econazole, ketoconazole, miconazole, oxiconazole, sulconazole, and combinations thereof.

18. The method of claim 16, wherein the triazole derivative is selected from the group consisting of itraconazole, fluconazole, terconazole, and combinations thereof.

19. The method of claim 16, wherein the allylamine comprises naftine.

20. The method of claim 16, wherein the allylamine comprises terbinafine.

21. The method of claim 1, wherein the implant comprises less than 30% active agent by weight.

* * * * *